US00PP14050P29

(12) United States Plant Patent
Trees

(10) Patent No.: US PP14,050 P2
(45) Date of Patent: Aug. 5, 2003

(54) VERBENA PLANT NAMED 'BALTUBLUE'

(75) Inventor: Scott C. Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/107,770

(22) Filed: Mar. 27, 2002

(51) Int. Cl.[7] ..... A01H 5/00
(52) U.S. Cl. ..... Plt./308
(58) Field of Search ..... Plt./308

*Primary Examiner*—Kent Bell
(74) *Attorney, Agent, or Firm*—Wood, Phillips, Katz, Clark & Mortimer

(57) ABSTRACT

A new and distinct Verbena plant named 'Baltublue', characterized by its violet flowers, spreading and trailing habit, and sharply lobed, dark green leaves.

2 Drawing Sheets

LATIN NAME OF GENUS AND SPECIES OF PLANT CLAIMED

*Verbena hybrida.*

VARIETY DENOMINATION

'Baltublue'.

BACKGROUND OF INVENTION

The present invention comprises a new and distinct verbena plant, botanically known as *Verbena hybrida*, and hereinafter referred to by the cultivar name 'Baltublue'.

The new cultivar was developed by the inventor in a controlled breeding program during 1998, at Arroyo Grande, Calif. The objective of the breeding program was the development of verbena cultivars with a spreading and trailing habit, continuous flowering, excellent basal branching and dark green foliage.

The female (seed) parent of 'Baltublue' was the verbena variety 'Summaref TP-V' U.S. Plant Pat. No. 9,411), which exhibits a trailing habit, dark purple flowers and medium green foliage. The male (pollen) parent of 'Baltublue' was the verbena variety Heirloom Light Blue (not known to be patented) which exhibits a semi-upright habit and light lavender flowers. 'Baltublue' was selected in September 1999 as a single flowering plant from within the progeny of the above stated cross and was initially designated 132-2.

Asexual reproduction of the new cultivar by terminal cuttings has demonstrated that the characteristics of the new cultivar as herein described are firmly fixed and retained through successive generations of such asexual propagation.

SUMMARY OF INVENTION

It was found that the cultivar of the present invention:

(a) Exhibits violet flowers;

(b) Forms sharply lobed, dark green foliage;

(c) Exhibits a good basal branching character; and (d) Exhibits a spreading and trailing growth habit.

The new cultivar of the present invention can be compared to 'Balazdapi' (U.S. Plant Pat. No. 12,807). In side by side comparison, plants of the new cultivar have smaller inflorescences and flowers of a lighter violet color than plants of 'Balazdapi'.

BRIEF DESCRIPTION OF PHOTOGRAPHS

The accompanying photographs show as nearly true as it is reasonably possible to make the same in color illustrations of this type, typical flower and foliage characteristics of the new cultivar. The plants were grown for approximately 10 weeks in a greenhouse at West Chicago, Ill.

The drawing on the first sheet depicts a side view of a plant of 'Baltublue'.

The drawing on the second sheet depicts a close-up view of typical flowers of 'Baltublue'.

DETAILED BOTANICAL DESCRIPTION

'Baltublue' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Feb. 15, 2002. The readings were taken between 1:00 and 3:00 p.m. under natural daylight conditions. The plants were produced from cuttings taken from stock plants and were grown in a double polycarbonate covered greenhouse in West Chicago, Ill. under conditions comparable to those used in commercial practice. The plants were grown for 15 weeks while utilizing a soilless growth medium and maintaining temperatures of approximately 70° to 80° F. (21° to 26° C.) during the day and approximately 62° to 65° F. (17° to 18° C.) during the night and light levels above 5,000 footcandles.

Classification:

*Botanical.*—*Verbena hybrida* cultivar 'Baltublue'.

Parentage:

*Female parent.*—'Sunmaref TP-V'.

*Male parent.*—Heirloom Light Blue.

Propagation:

*Type cutting.*—Terminal tip.

*Time to initiate roots.*—Approximately 14–21 days with the shorter times generally being experienced in the summer and the longer times in the winter.

*Root description.*—Fibrous, branching.

Plant description:

*Habit of growth.*—Moderately vigorous with good basal branching. Pinching improves basal branching. A mature plant, 15 weeks after the planting of a rooted cutting, measures approximately 12.8 cm in height and approximately 26.6 cm in width.

*Form.*—Mounded, trailing and spreading.

*Stem.*—Tetragonal, approximately 37.5 cm in length and 2 mm in diameter, with dense pubescence. Color is 144A. Internode length at middle of stem is approximately 4.4 cm. Roots form at internodes.

*Foliage.*—Leaves are opposite, ovate with sharply lobed margin, acute apex and attenuate base. Upper surface is densely covered with short, stiff hairs. Lower surface is sparsely covered with short stiff hairs while the veins are densely pubescent. Approximately 2.7 cm in length and approximately 2.2 cm at widest point. Upper surface is 137B, lower surface is 137D. Upper and lower surfaces have pinnate-reticulate venation. Color of venation on upper surface is 145B. Color of venation on lower surface is 137D. Petiole surface is densely pubescent, length is approximately 7 mm, diameter is 2 mm and color is 145D.

Flowering description:

*Flowering habit.*—Freely flowering.

*Natural flowering season.*—Year round in greenhouse environment and spring through autumn in outdoor garden.

*Lastingness.*—Flowers last about 10–14 days on the plant.

*Inflorescence type.*—Corymb. Approximately 2.2 cm deep and approximately 4.2 cm in diameter with approximately 16.7 fully open flowers per inflorescence at any one time.

*Peduncle.*—Length is approximately 7.2 cm and diameter is approximately 1 mm. Color is 146C.

*Bud.*—Round, approximately 3 mm in diameter and 90C in color.

*Petals.*—Five, fused at base, non overlapping, flat, obovate in shape, emarginate apex, and entire margin.

*Corolla.*—Diameter is approximately 1.4 cm. Corolla tube length is approximately 1.7 cm.

*Sepals.*—Five, fused to form calyx. Calyx is approximately 1 cm in length and 2 mm in diameter. Outer surface of the calyx is densely pubescent with glands of 86A and the inner surface is smooth. Sepal apex is acuminate, margin is entire, and upper and lower surface color is 143B.

*Flower color.*—Darker than 88A when first opening. Fully opened, upper surface: 88B with midvein of 82A. Fully opened, lower surface: 90D at edges, gradually fading to 77D at base. Whiskers of 91A surround the opening of the corolla tube.

*Reproductive organs.*—There are 4 stamens fused to the corolla tube. Two are positioned above the stigma and two are positioned below the stigma. The anther length is approximately 1 mm and the color is 145A. Pollen was not observed. There is one pistil, 1.4 cm in length. The stigma length is approximately 2 mm and the color is 144B. The style length is approximately 1.1 cm and the color is 145B. Ovary length is approximately 1 mm and 144A.

Seed production: Seed production has not been observed.

Disease resistance: Resistance to pathogens has not been observed to date.

Hardiness zone: 'Baltublue' is hardy in zones eight (8) and above.

I claim:

1. A new and distinct cultivar of *Verbena hybrida* plant named 'Baltublue' substantially as herein shown and described, which:

(a) Exhibits violet flowers;

(b) Sharply lobed, dark green foliage;

(c) Exhibits a good basal branching character; and (d) Exhibits a spreading and trailing growth habit.

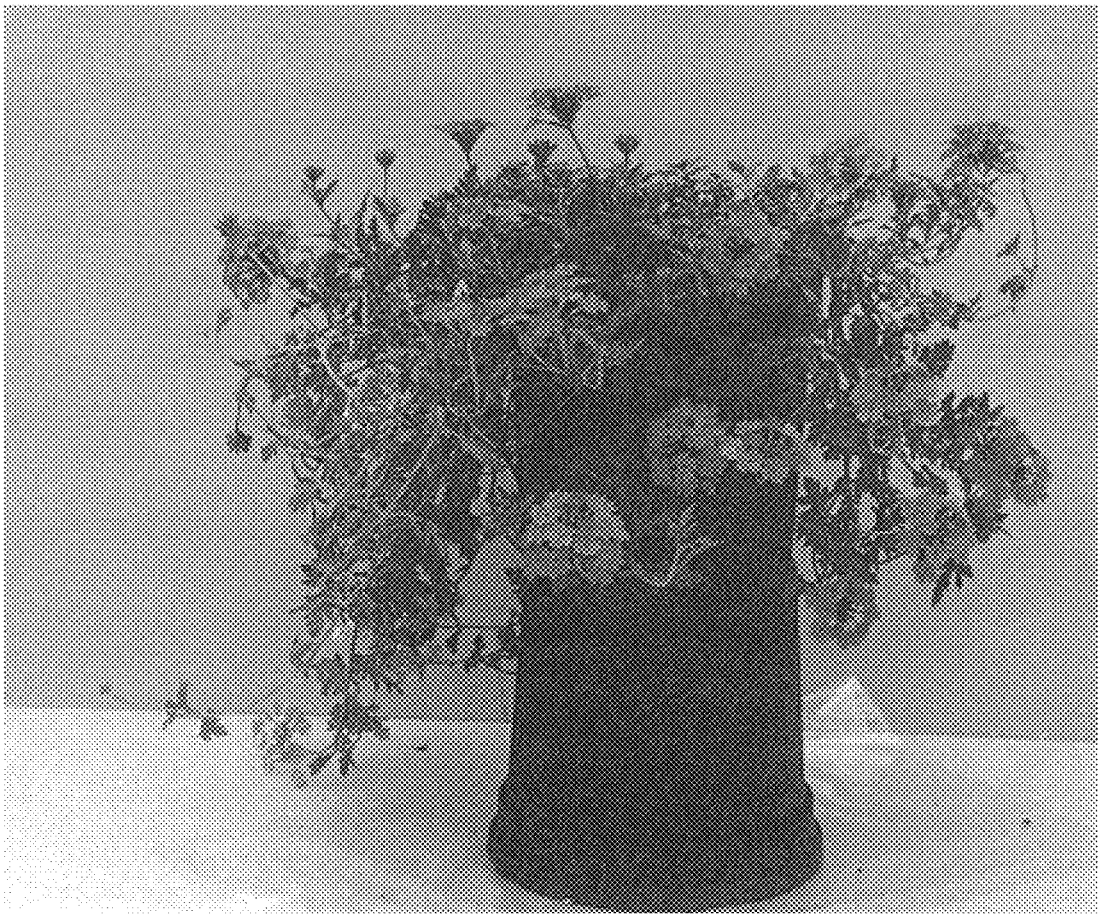

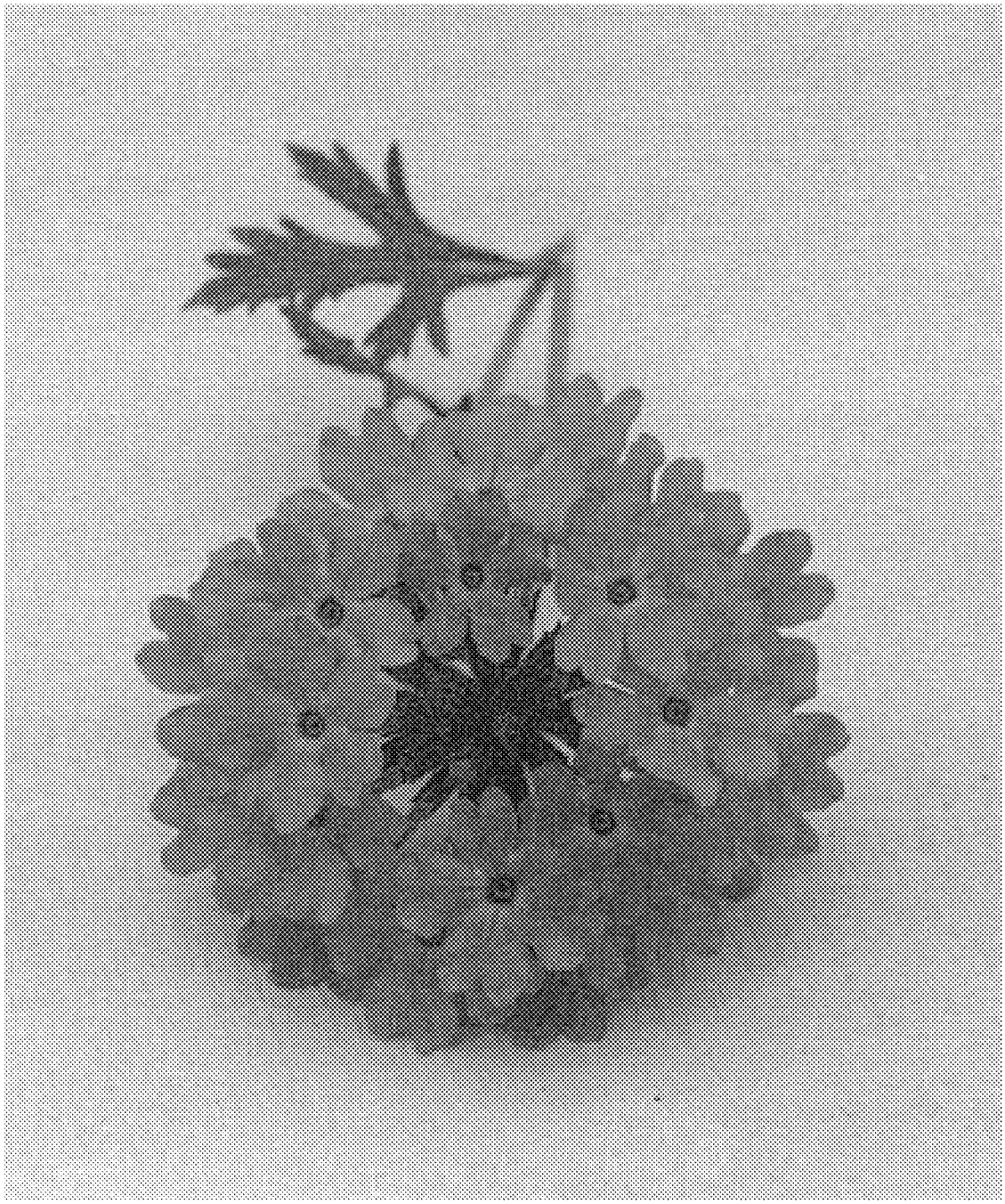

* * * * *